(12) United States Patent  (10) Patent No.: US 8,806,683 B2
Gauta                      (45) Date of Patent: Aug. 19, 2014

(54) PORTABLE STIRRUP WITH LEG SUPPORT

(71) Applicant: Joseph Gauta, Naples, FL (US)

(72) Inventor: Joseph Gauta, Naples, FL (US)

(*) Notice: Subject to any disclaimer, the term of this patent is extended or adjusted under 35 U.S.C. 154(b) by 0 days.

(21) Appl. No.: 13/906,923

(22) Filed: May 31, 2013

(65) Prior Publication Data
US 2013/0318721 A1    Dec. 5, 2013

Related U.S. Application Data

(60) Provisional application No. 61/654,582, filed on Jun. 1, 2012.

(51) Int. Cl.
A61G 15/12    (2006.01)
A61G 13/12    (2006.01)
A61F 5/37     (2006.01)

(52) U.S. Cl.
CPC .......... *A61G 13/1245* (2013.01); *A61G 13/125* (2013.01); *A61G 13/128* (2013.01); *A61F 5/3761* (2013.01)
USPC ............. 5/624; 5/621; 5/630; 5/648; 5/649; 5/651

(58) Field of Classification Search
USPC ............ 5/621, 624, 630, 648, 649, 651, 658, 5/661
See application file for complete search history.

(56) References Cited

U.S. PATENT DOCUMENTS

| | | | |
|---|---|---|---|
| 2,067,891 A | 1/1937 | Comper | |
| 2,844,143 A * | 7/1958 | Swanson | 602/36 |
| 4,186,738 A * | 2/1980 | Schleicher et al. | 128/892 |
| 4,221,370 A * | 9/1980 | Redwine | 5/613 |
| 4,373,709 A | 2/1983 | Whitt | |
| 4,407,277 A | 10/1983 | Ellison | |
| 4,426,071 A * | 1/1984 | Klevstad | 5/602 |
| 4,428,571 A | 1/1984 | Sugarman | |
| 4,526,355 A | 7/1985 | Moore et al. | |
| 4,564,164 A * | 1/1986 | Allen et al. | 248/118 |
| 4,615,516 A * | 10/1986 | Stulberg et al. | 5/650 |
| 4,717,133 A | 1/1988 | Walsh et al. | |
| 4,776,108 A * | 10/1988 | Bayless | 36/1 |
| 4,809,687 A * | 3/1989 | Allen | 602/4 |
| 4,940,218 A * | 7/1990 | Akcelrod | 5/621 |
| 5,104,363 A * | 4/1992 | Shi | 482/73 |
| 5,369,827 A * | 12/1994 | Parke et al. | 5/649 |
| 5,507,050 A * | 4/1996 | Welner | 5/600 |
| 5,560,577 A * | 10/1996 | Keselman | 248/279.1 |
| D385,040 S * | 10/1997 | Keselman | D24/192 |
| 6,263,531 B1 * | 7/2001 | Navarro et al. | 5/648 |
| 7,337,483 B2 * | 3/2008 | Boucher et al. | 5/621 |
| 7,351,216 B2 * | 4/2008 | Walsh | 602/33 |
| 2007/0265635 A1 | 11/2007 | Torrie et al. | |
| 2008/0120756 A1 | 5/2008 | Shepherd | |
| 2009/0235457 A1 | 9/2009 | Harvey | |
| 2012/0233782 A1 * | 9/2012 | Kreuzer et al. | 5/624 |
| 2012/0305006 A1 * | 12/2012 | Keith-Lucas et al. | 128/845 |

* cited by examiner

*Primary Examiner* — William Kelleher
*Assistant Examiner* — David R Hare
(74) *Attorney, Agent, or Firm* — McHale & Slavin, P.A.

(57) ABSTRACT

A portable boot style stirrup assembly with leg support for use during medical procedures. The portable boot style stirrup assembly affixes to the existing stirrup footrests found about medical examination tables, resultantly increasing procedural efficiency and decreasing doctor cost of the performance of in-office medical procedures, increasing patient comfort during prolonged procedures, and increasing doctor and patient safety during procedures. The portable boot style stirrup assembly includes a boot shell structure which supports a patient's foot and calf and a receptacle constructed and arranged to receive the existing stirrup footrest of medical procedure tables and allow for adjustment of the adductive and abductive angle positioning of a patient's leg for examination and surgical procedures.

9 Claims, 7 Drawing Sheets

PORTABLE STIRRUP WITH LEG SUPPORT

PRIORITY CLAIM

In accordance with 37 C.F.R. 1.76, a claim of priority is included in an Application Data Sheet filed concurrently herewith. Accordingly, the present invention claims priority under 35 U.S.C. §119(e), 120, 121, and/or 365(c) to U.S. Provisional Patent Application No. 61/654,582, entitled "PORTABLE STIRRUP WITH LEG SUPPORT", filed Jun. 1, 2012. The contents of which the above referenced application is incorporated herein by reference.

FIELD OF THE INVENTION

This invention is directed to the medical field and more particularly to a portable stirrup with leg support for the temporary securement of a patient's foot and leg to a table while undergoing an examination, a procedure, or surgery.

BACKGROUND OF THE INVENTION

In the medical fields of obstetrics and gynecology medical doctors typically employ an examination table in order to place a patient in a comfortable position when performing a medical examination or procedure. An example where examination is best performed in a supine or lithotomy position is in the performance of a gynecological, urological, and proctologic examination.

Examination tables in these fields typically have footrests protractible from the examination table. A common type of footrest coupled to an examination table is known as the stirrup style footrest. The stirrup footrest allows a patient positionably lying on the examination table to rest their feet against the support of the footrest. For example, a woman positionably lying supine in the dorsal lithotomy position on the examination table would rest both of her feet against the two stirrups with bent knees during a Pap smear or other procedure. A problem with the typical stirrup footrest type support is that it can be uncomfortable when a patient positions their feet against the stirrup footrest for an extended period of time. A Pap smear or annual gynecologic exam may take approximately five to twenty-five minutes which can be a long time to hold your feet in a particular position. Other procedures can take longer amounts of time.

Office-based medical procedures further allow doctors to employ the use of such tables for minor surgery in an office setting such as Endometrial Ablation, LEEPs, Cystoscopy, Colposcopy, Cosmetic Vulvar Surgery, leg surgeries, ultrasound, lithotomies, fracture repairs, and so forth. Specifically, the current examination tables limit the ability for a doctor to execute prolonged medical procedures. Also the current examination tables do not provide a comfortable boot style footrest that may be used with a variety of examination tables. More specifically, the examination tables in medical offices are typically not configured to provide foot and leg support for a person lying with their feet held against the stirrups for a prolonged period of time.

Various devices are taught in the prior art for supporting the leg of a patient during surgical procedures. Illustrative of such devices are disclosed in U.S. Pat. No. 4,373,709; U.S. Pat. No. 4,407,277; U.S. Pat. No. 4,428,571; U.S. Pat. No. 4,526,355; U.S. Pat. No. 4,615,516; U.S. Pat. No. 4,717,133; U.S. Pat. No. 5,369,827 and U.S. Publication No. 2009/0235457 A1.

The Harvey Stirrups™ and the Allen® Stirrups are currently the more common stirrups used in conjunction with examination tables today. However, the existing boot style stirrups currently found in medical offices are lacking portability, adjustability, comfort, and are relatively expensive. Some current stirrups need to be permanently attached to an exam table effectively destroying portability and requiring an additional set of stirrups for each examination table. For instance a gynecologic exam table may cost about $1000 and conventional stirrups may cost $2000-$6000 in current dollars. Further, once the conventional stirrups are attached to an examination table a patient must employ them if they are to use the footrests. Therefore there exists a need for a boot style stirrup footrest that can quickly and easily be attached to existing examination tables when stirrups are needed, moved from table to table, or stored when not in use.

What is needed is a portable and adjustable device that will not move inadvertently during medical procedures.

SUMMARY OF THE INVENTION

The instant invention addresses the above need by providing a portable leg support that improves a conventional examination table by use of boot style stirrups capable of supporting the weight of a patient's foot and leg, thereby providing increased support for resting both the feet and legs during a prolonged period of examination or operation.

The portable leg support of the instant invention includes a pair of boot style stirrups with a receiving portion, the receiving portion capable of receiving the existing stirrup footrests located about an examination table. The boot style stirrups are one piece molded-plastic foot and calf braces capable of supporting patients up to 300 lbs.

In an advantageous embodiment, the receiving portion is a receptacle made to slip over or slip around or otherwise secure to the existing stirrup footrests. The boot style stirrups will include straps to secure the patient's foot and leg. The receiving portion may fit snugly to the stirrup footrest and provides a means to secure the stirrup footrest against the boot style stirrups.

The instant invention reduces the cost associated with permanent boot style stirrups because portable boot style stirrups may be used on an unlimited number of cooperating existing stirrup footrests, whereas, permanent boot style stirrups would require installation of such stirrups on each applicable examination table. The instant invention reduces patient movement during performance of medical office procedures because the patient may be more comfortable than with conventional stirrup footrests and because the patient may be secured to the boot style stirrup.

It is an objective of the invention to provide a portable stirrup that can be readily moved from table to table. The stirrup does not require altering existing equipment and universally fits over almost any existing stirrup footrest in the market and easily locks into place providing optimal support. This boot style stirrup allows for the use of the current examination tables in a doctor's office, without the need for alteration or the need to buy a different style exam table with a different style stirrup attachment (e.g., Allen® Stirrups).

Yet a further objective of the invention is to increase procedure efficiency by use of a device that can quickly stabilize a patient's leg position thereby making examination or medical procedures safer to the patient and physician.

Still another objective of the invention is to provide a portable boot style stirrup that can be easily removed from view to make the examination room cleanlier and easier to clean.

Yet another objective of the invention is to lower the stress level of patients that are receiving consultation regarding a procedure while in the examination room.

Yet still another objective of the invention is to provide a device that will allow adjustment of the adductive and abductive angle of a patient's leg and hip.

Another objective of the invention is to provide a foot stirrup that will provide for the separation of a patient's legs in a controlled manner allowing orthogonal adjustment for optimum leg positioning for examination and surgical procedures.

It is another objective of the invention to provide a portable boot style stirrup that can be easily stored when not in use and readily secured to a table when needed, without the need for alteration of the exam table.

The advantages of this invention include the providing of a device which causes the patient to be motionless, prohibits a patient's legs from slipping and hurting the patient should the patient fall asleep during the procedure; permits a physician to position a patient's feet and legs in different arrangements as necessary to accomplish different procedures; provide an attachment mechanism to secure the position of the leg when appropriate positioning is obtained; prevents a patient from accidentally kicking a service provider; provides a device that can be cleaned and/or sterilized for reuse.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DESCRIPTION OF THE INVENTION

Figure 1:
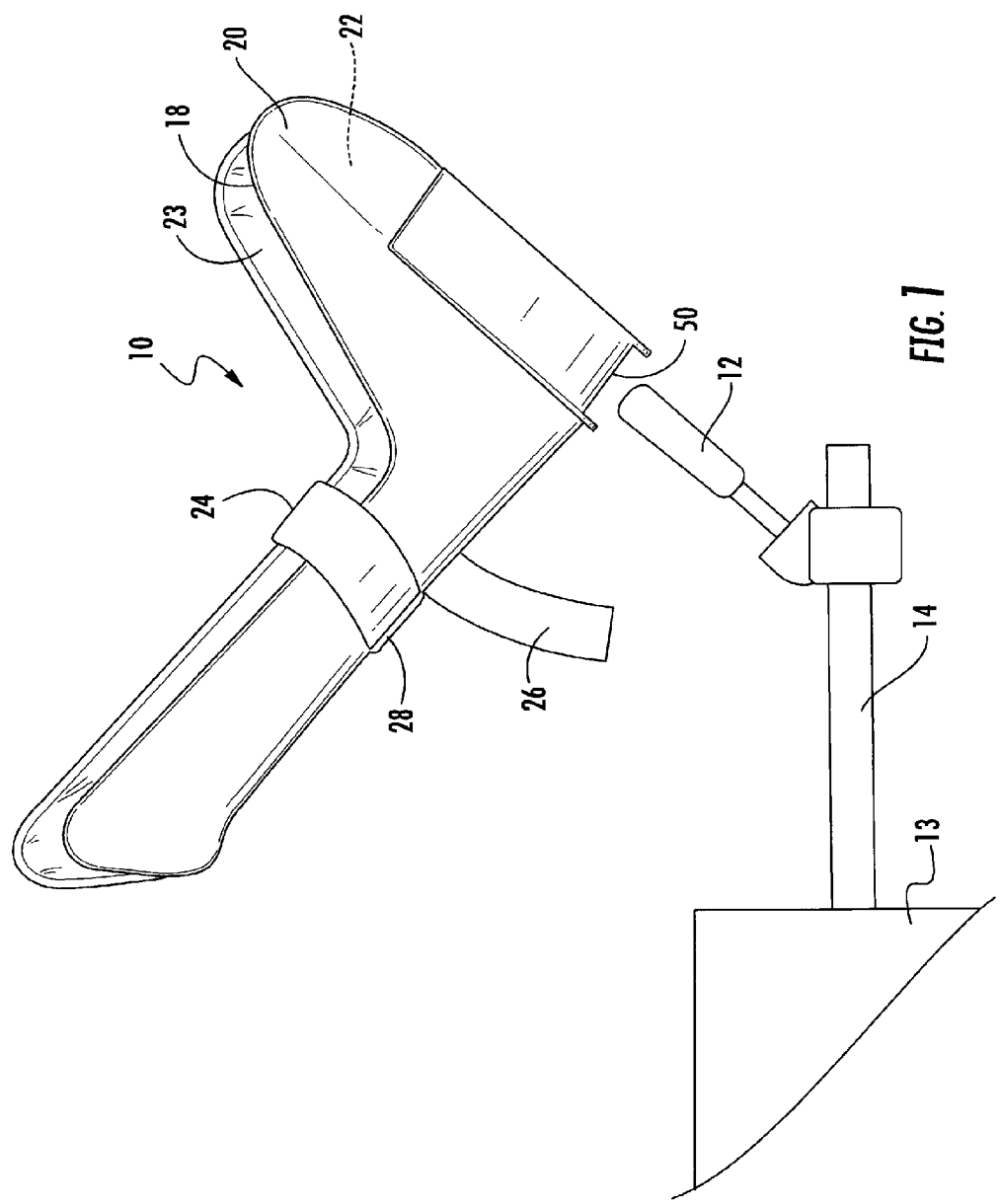
FIG. 1 is a perspective view of the stirrup assembly of the instant invention with a conventional operating/examination table and existing stirrup footrest.
Figure 2:
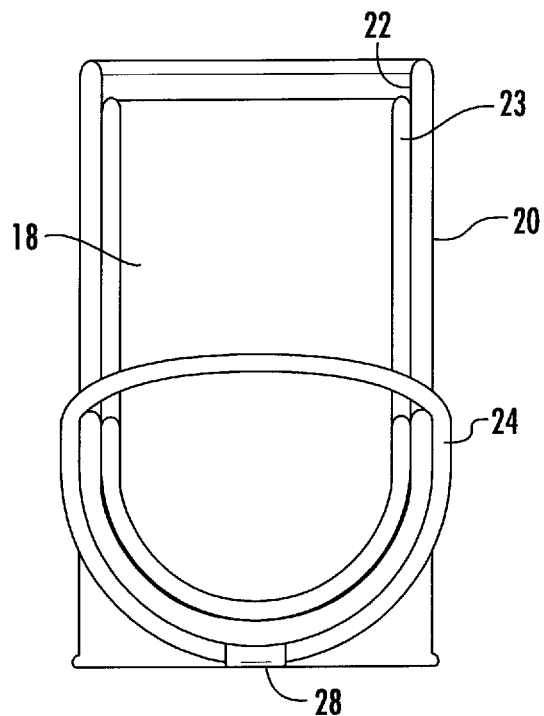
FIG. 2 is a top view of the boot assembly.
Figure 3:
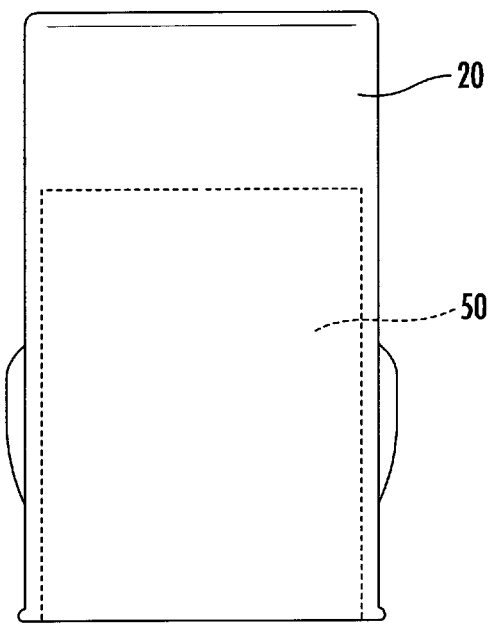
FIG. 3 is a bottom view of the boot assembly.
Figure 4:
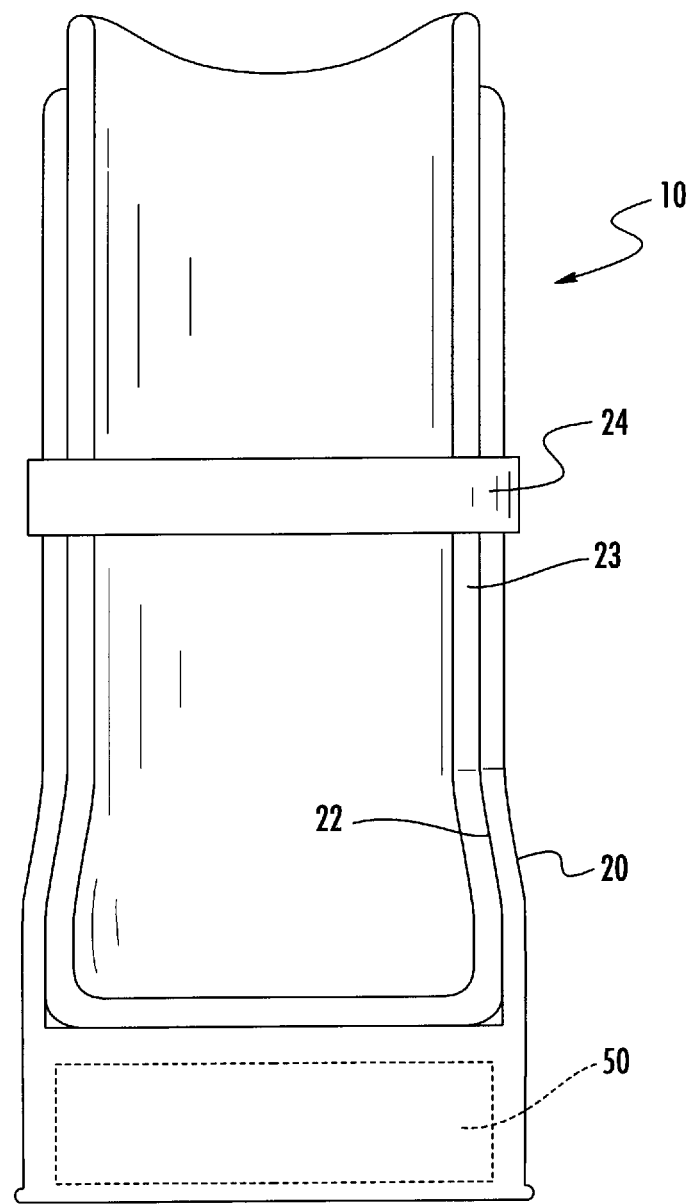
FIG. 4 is a front view of the boot assembly.

Referring now to the figures in general, set forth is a portable boot style stirrup assembly (10) which is securable to an existing stirrup footrest (12) found on a conventional examination and/or operating table (13). The portable boot style stirrup assembly (10) of the instant invention provides support about the heel and the calf of a patient allowing a patient to comfortably maintain position while lying supine in the dorsal lithotomy position throughout a medical procedure. The portable boot style stirrup assembly (10) is constructed as a rigid shell structure (18) preferably constructed from plastic. The shell structure (18) has an outer surface (20) and an inner surface (22) with an open front shaped to conform to a foot and calf of a patient, the inner surface is preferably padded by use of a shell liner (23) for providing comfort to a barefoot patient. The liner (23) can be constructed from a disposable material, such as open cell foam that can be used once and disposed of. Alternatively the liner (23) may be constructed from a reusable material, such as closed cell foam, capable of repeated sterilizations. The liner (23) can made of a "one size fits all" wherein the shell structure has flexibility along each side wall surface to allow compression around the ankles. Alternatively the liner can be constructed from different thicknesses to accommodate various size feet wherein minimal or no flexibility of the shell side wall surface is required to secure the patient's foot.

Adjustable straps (24) are attached to the shell structure (18) for securing the patient's foot therein, either by causing deformation of the side wall surface or by simply belting wherein the strap (24) holds the liner (23) and the foot placed therein. The straps (24) may consist of a buckle, snap, hook and loop fastener (Velcro), or the like equivalent having an objective of securing the foot to the shell structure (18). The straps (24) may connect to the portable boot style stirrup assembly (10) on the outer side wall surface (20) near the calf of the patient through a D shaped ring (28) securing the strap (24) in place.

An advantage of the portable boot style stirrup assembly (10) is that it does not require altering of existing equipment (12 and 13) and will universally fit over and engage with most any existing stirrup footrests (12) currently in the market. This allows the attending individual to adjust the existing stirrup footrest (12) without modification. The portable boot style stirrup assembly (10) is designed to be easily removed from the existing stirrup footrest (12), and where a reusable liner and shell is employed, can be placed in an equipment washer for cleaning.

The portable boot style stirrup assembly (10) is attached to an existing stirrup footrest (12) by use of a receptacle (50) constructed and arranged to receive the existing stirrup footrest (12). The receptacle (50) is formed from a cavity having a top surface (52), a bottom surface (54), a right side surface (56), a left side surface (58), and a front surface (60). The receptacle is located in a heel position of the shell structure (18). The top surface (52) of the receptacle (50) is spaced sufficiently apart from the bottom surface (54) with the spacing up to twice the size of the existing conventional stirrup footrests (12) so that most any existing stirrup footrest (12) will fit between the top surface (52) and the bottom surface (54) and allow the shell structure (18) to tilt or rotate a predetermined amount about the existing footrest stirrup (12). The spacing allows for the adjustment of the degree of fore and aft angle of a patient's leg along with the degree of adduction and abduction of the patient's leg. A strap, either the same strap (24) as used to secure the patient's foot and leg to the shell structure (18) or an additional adjustable strap (26) can attach the portable boot style stirrup assembly (10) from the D-ring (28) or the sides of the receptacle (50) to the existing stirrup footrest member arm (14) or existing stirrup footrest (12), which can be used to secure the portable boot style stirrup assembly (10) to the existing stirrup footrest (12).

Figure 5:
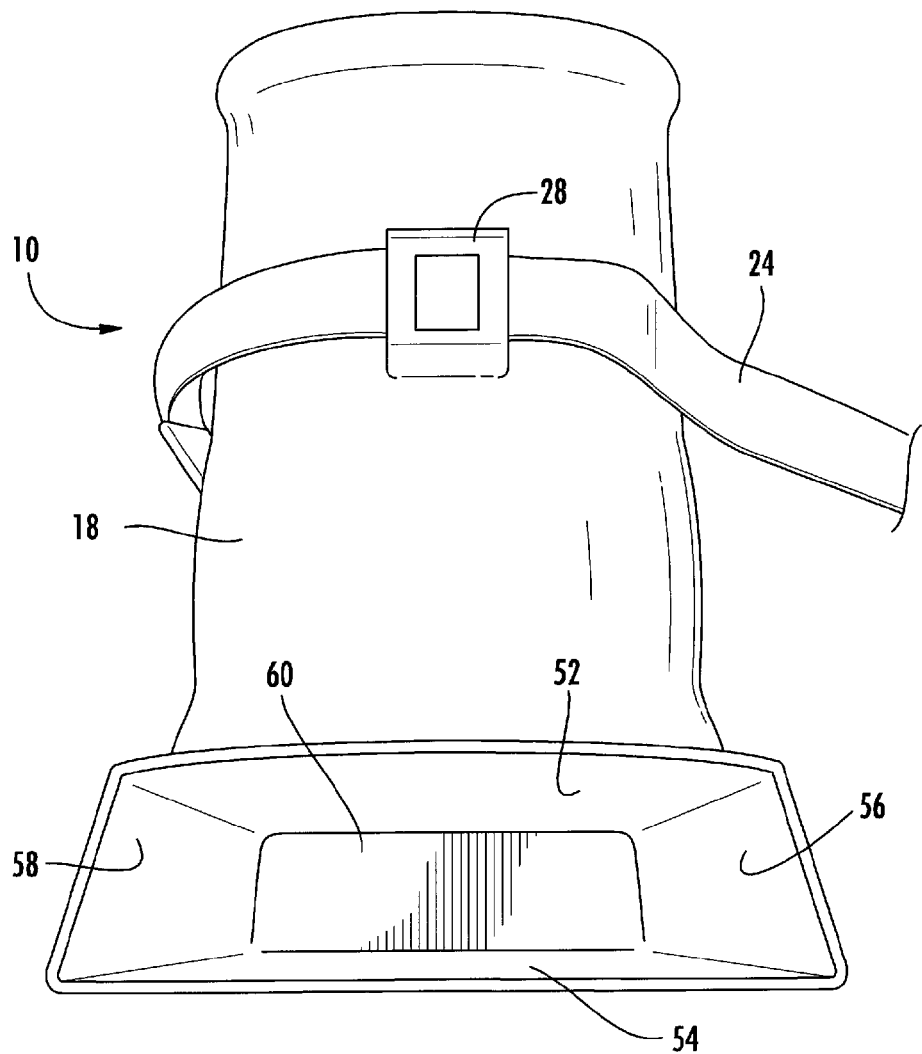
FIG. 5 is a rear view of the boot assembly.
Figure 6:
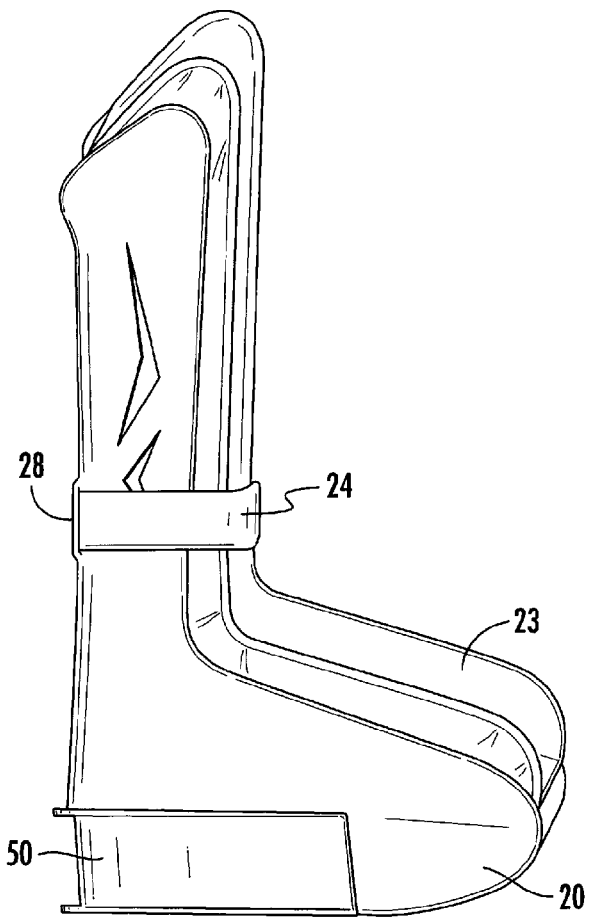
FIG. 6 is a left side view of the boot assembly.
Figure 7:
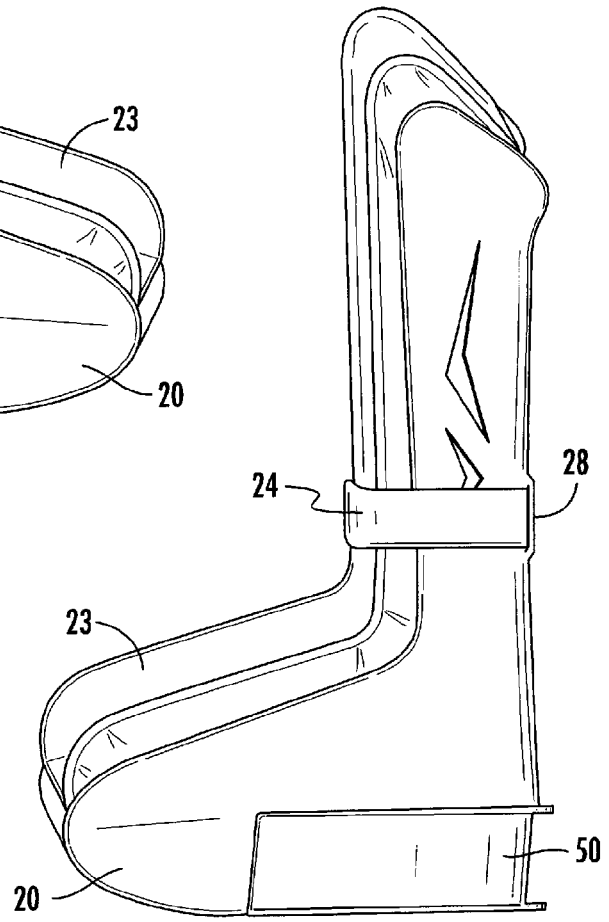
FIG. 7 is a right side view of the boot assembly.
Figure 8:
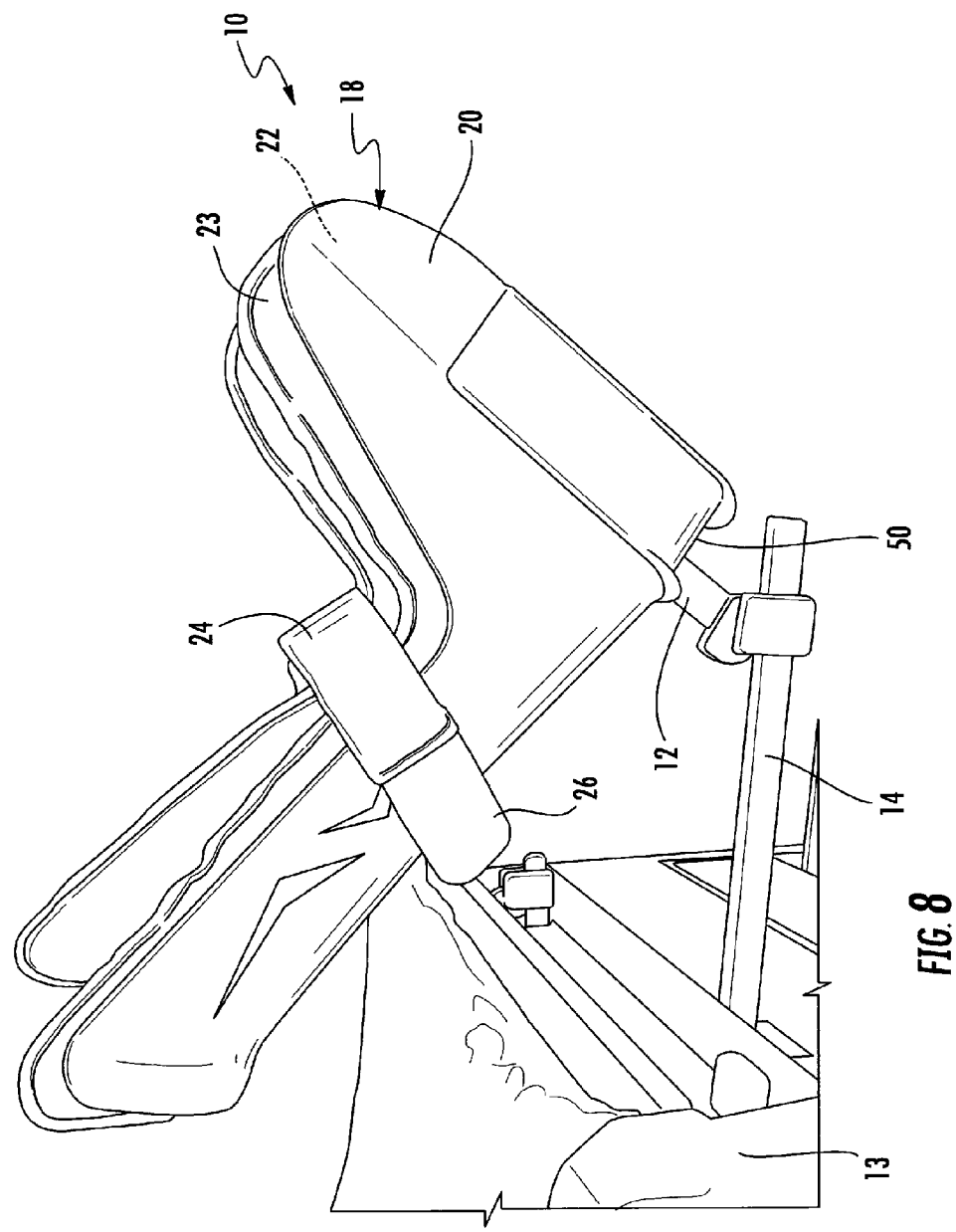
FIG. 8 is a pictorial view of how the boot assembly engages with a conventional footrest.
Figure 9:
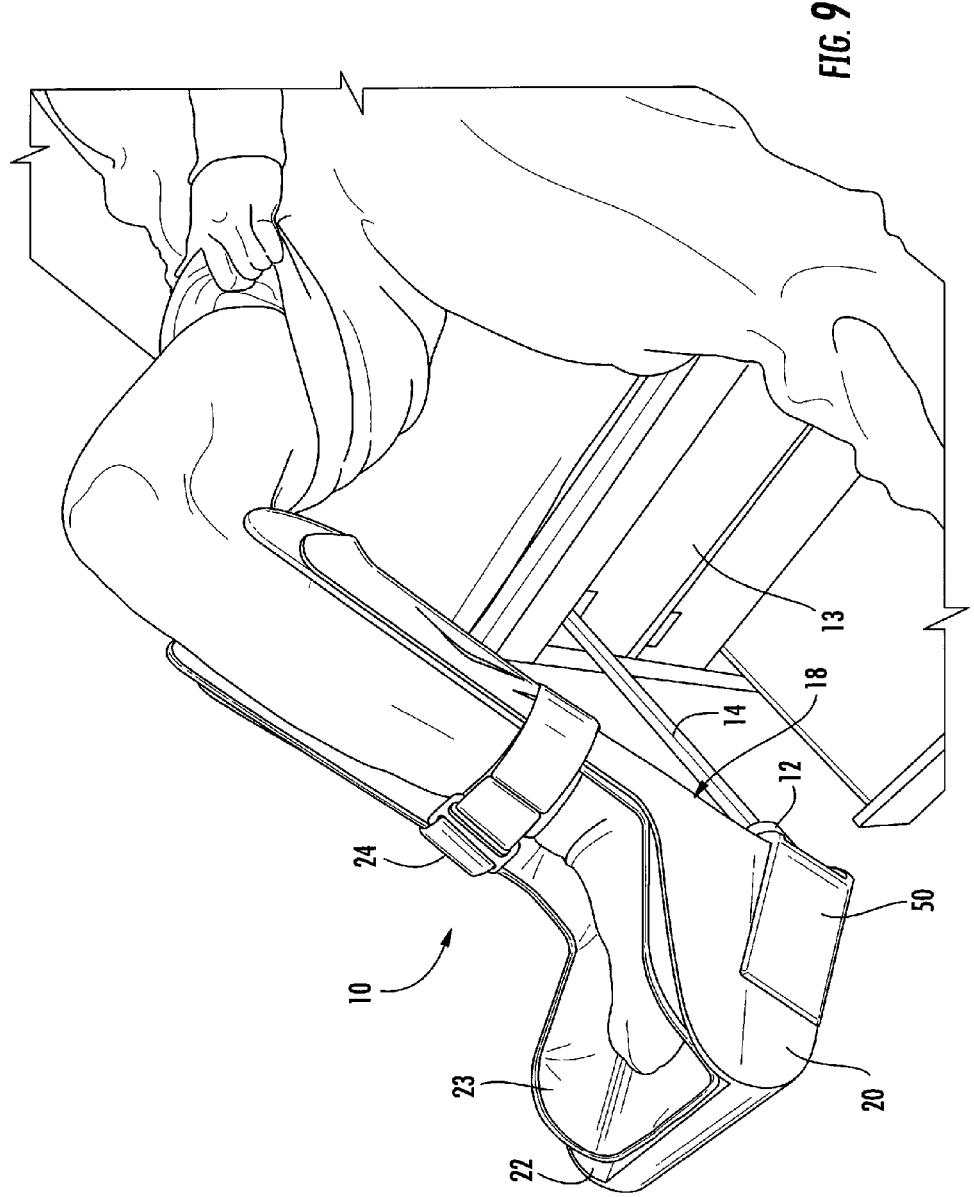
FIG. 9 is a pictorial view of how the boot assembly engages with a conventional footrest and the leg of a patient.

As shown in FIG. 5, the receptacle (50) has a top surface (52), a bottom surface (54), a right side surface (56), a left side surface (58), and a front surface (60), all of which bound the existing stirrup footrest (12) when the portable boot style stirrup assembly (10) is engaged with the existing stirrup footrest (12).

All patents and publications mentioned in this specification are indicative of the levels of those skilled in the art to which the invention pertains. All patents and publications are herein incorporated by reference to the same extent as if each individual publication was specifically and individually indicated to be incorporated by reference. It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A portable boot securable to a conventional medical exam table stirrup footrest comprising:
   a shell structure defined by a back wall, opposing left and right side walls, and a lower wall forming an interior area constructed and arranged to receive a human foot, a receptacle integrated within the shell structure and located in a heel section of the shell structure, said receptacle positioned in said lower wall forming an opening along the heel section of said shell, said receptacle including a top surface extending along a length of said lower wall terminating in a front surface, a left side surface and a right side surface depending from said lower wall to a bottom wall, said receptacle constructed and arranged to receive a conventional stirrup footrest and allow adjustment for adduction and abduction of a patient's leg placed within said shell structure without movement of the stirrup footrest, wherein said receptacle allows said shell structure to engage with and secure to a conventional footrest stirrup by insertion of the stirrup through the receptacle opening, said receptacle sized to receive the stirrup no further than said front surface and allow fore and aft rotation by angular rotation of said shell structure about said footrest stirrup without movement of the stirrup footrest.

2. The shell structure of claim 1 wherein said front side of the shell structure is predominantly U-shaped to cradle the foot, ankle and calf of an individual.

3. The shell structure of claim 2 wherein said left and right side walls are flexible and conform to the shape of a human foot.

4. The shell structure of claim 1 including a first strap used to secure said shell structure to the calf of an individual whereby said shell structure is estopped from disengaging the foot during use.

5. The shell structure of claim 4 further comprising an integrally formed D-ring or connector on said back side of said shell structure, wherein said strap will be secured to said shell structure to prevent movement of said strap during use of said portable boot stirrup.

6. The shell structure of claim 1 further comprising a second strap coupled to said D-ring or connector or to said receptacle, wherein said second strap can be used to secure said portable boot style stirrup assembly to a table to which said existing stirrup footrest is coupled.

7. The shell structure of claim 1 including a foam liner positionable within said shell structure.

8. The shell structure of claim 7 wherein said liner is constructed from a closed cell foam and can be washed and sterilized for reuse.

9. The shell structure of claim 7 wherein said liner is constructed from disposable open cell foam.

\* \* \* \* \*